United States Patent [19]
Ludwig et al.

[11] Patent Number: 5,427,798
[45] Date of Patent: Jun. 27, 1995

[54] CONTROLLED SUSTAINED RELEASE TABLETS CONTAINING BUPROPION

[75] Inventors: Jennie Sue G. Ludwig, Greenville; William L. Bass, Jr., Farmville; Joel E. Sutton, Jr., Greenville, all of N.C.

[73] Assignee: Burroughs Wellcome Co., Research Triangle Park, N.C.

[21] Appl. No.: 105,447

[22] Filed: Aug. 12, 1993

[30] Foreign Application Priority Data

Aug. 14, 1992 [GB] United Kingdom ............... 9217295

[51] Int. Cl.$^6$ .................................................. A61K 9/22
[52] U.S. Cl. .................................... 424/464; 424/465; 424/468; 424/474; 514/772; 514/781; 514/960; 514/970
[58] Field of Search .............. 424/464, 465, 468, 474

[56] References Cited

U.S. PATENT DOCUMENTS

| | | | |
|---|---|---|---|
| Re. 33,994 | 7/1992 | Baker et al. | 424/465 |
| 3,819,706 | 6/1974 | Mehta | 260/570.5 |
| 3,855,046 | 5/1975 | Mehta | 424/330 |
| 3,885,046 | 5/1975 | Mehta | 424/330 |
| 4,347,176 | 8/1982 | Mehta | 260/112 B |
| 4,347,177 | 8/1982 | Phillips | 260/112 |
| 4,347,178 | 8/1982 | Findlay et al. | 260/112 |
| 4,347,257 | 8/1982 | Stern | 424/330 |
| 4,347,382 | 8/1982 | Scharver | 564/183 |
| 4,355,179 | 10/1982 | Findlay et al. | 564/177 |
| 4,356,165 | 10/1982 | Findlay | 424/1 |
| 4,393,078 | 7/1983 | Peck | 424/330 |
| 4,425,363 | 1/1984 | Stern | 424/330 |
| 4,435,449 | 3/1984 | Stern | 424/330 |
| 4,438,138 | 3/1984 | Stern | 424/330 |
| 4,507,323 | 3/1985 | Stern | 514/649 |
| 4,571,395 | 2/1986 | Peck | 514/221 |
| 4,687,660 | 8/1987 | Baker et al. | 424/465 |
| 4,769,027 | 9/1988 | Baker et al. | 424/493 |
| 4,798,826 | 1/1989 | Peck | 514/221 |

FOREIGN PATENT DOCUMENTS

| | | |
|---|---|---|
| 0467488A2 | 1/1922 | European Pat. Off. |
| 0171457A1 | 2/1986 | European Pat. Off. |
| 92/19226 | 11/1992 | WIPO |

OTHER PUBLICATIONS

Dow Chemical Company Catalog; Formulating for Controlled Release with METHOCEL premium cellulose ethers; pp. 1-32., Oct. 1989.

*Primary Examiner*—D. Gabrielle Phelan
*Assistant Examiner*—James M. Spear
*Attorney, Agent, or Firm*—Donald Brown; Lawrence A. Nielsen

[57] ABSTRACT

A controlled sustained release tablet having at least one year shelf life and containing bupropion hydrochloride, hydroxypropyl methylcellulose and cysteine hydrochloride or glycine hydrochloride with the tablet having a surface area to volume ratio to effectively control bupropion hydrochloride release in the body.

19 Claims, 4 Drawing Sheets

CONTROLLED SUSTAINED RELEASE TABLETS CONTAINING BUPROPION

BACKGROUND OF THE INVENTION

Bupropion hydrochloride (Wellbutrin ®) is a marketed antidepressant. It is chemically known as (±)-2-(tert-butylamino)-3'-chloropropiophenone hydrochloride. (See U.S. Pat. Nos. 3,819,706 and 3,885,046 and the Merck Index, Eleventh Edition, entry No. 1488).

In usage, bupropion hydrochloride is sold in the form of an instant release tablet wherein greater than 75% of bupropion hydrochloride is released from the tablet into dissolution media in 45 minutes (See 1993 Physicians Desk Reference (PDR), pages 842 to 844). The PDR indicates bupropion hydrochloride as presently sold in an instant release tablet as being associated with seizures in approximately 0.4% (4/1000) patients treated at doses of up to 450 mg per day. In studies to date, the risk of seizures seem to be strongly associated, in part, with use of instant release tablets.

In order to reduce the seizure rate, it has been determined after experimentation that a controlled sustained release of bupropion hydrochloride should be employed.

Prior art with respect to this invention is to be found in U.S. Pat. No. 4,687,660 which discloses controlled sustained release tablets containing bupropion hydrochloride.

The present invention provides an improved product as well as ease of manufacture over that disclosed in U.S. Pat. No. 4,687,660.

After almost three years of work and testing, the present invention is now able to provide a controlled sustained release, sometimes also referred to as a sustained release (SR) tablet with improved properties and which has a shelf life over one year (i.e., there is less than 10% loss, most preferably less than about 5% loss (breakdown), of bupropion hydrochloride in one year) of storage at room temperature (59° to 77° C.) and 35 to 60% relative humidity. For example, with a tablet containing 100 mg of bupropion hydrochloride (label strength) the tablet will preferably contain no less than about 95 mg of bupropion hydrochloride after one year in storage (shelf life). As used herein, the term "tablet" includes the term "caplet", which is the word used to describe a tablet termed substantially in the shape of a capsule.

The oral administration of the controlled release tablets of this invention to treat depression in humans will be under the jurisdiction of the physician; however, tablets for a 150 pound human will ordinarily be given one to three times per day to provide a total daily dosage of 100 to 450 mg per day for a time period that the human patient requires same as determined by a physician. The tablets are swallowed by the human in the normal manner with the aid of water or other liquid. The tablets herein preferably have a round biconvex shape (which is preferred); however, this may be varied depending on the creativity of the tablet designer. With the tablets of this invention it is now possible to dose one or two times per day rather than the three times a day as presently done with the currently marketed product.

BRIEF STATEMENT OF THE INVENTION

This invention is directed to control sustained release (SR) tablets containing bupropion hydrochloride (as the drug or active ingredient), preferably hydroxypropyl methylcellulose (Methocel ®) for controlling drug release rate, and cysteine hydrochloride or glycine hydrochloride. Cysteine hydrochloride is more preferable than glycine hydrochloride, since it unexpectedly causes less discoloration to the tablet core. The amount of bupropion hydrochloride in each tablet is typically from 25 mg to 500 mg, with the tablet dose being more typically 50 mg, 100 mg or 150 mg.

Methocel ® is the brand name for hydroxypropyl methylcellulose (HPMC) from Dow Chemical. Other companies also supply HPMC.

A BRIEF DESCRIPTION OF THE DRAWINGS

Figure 4:
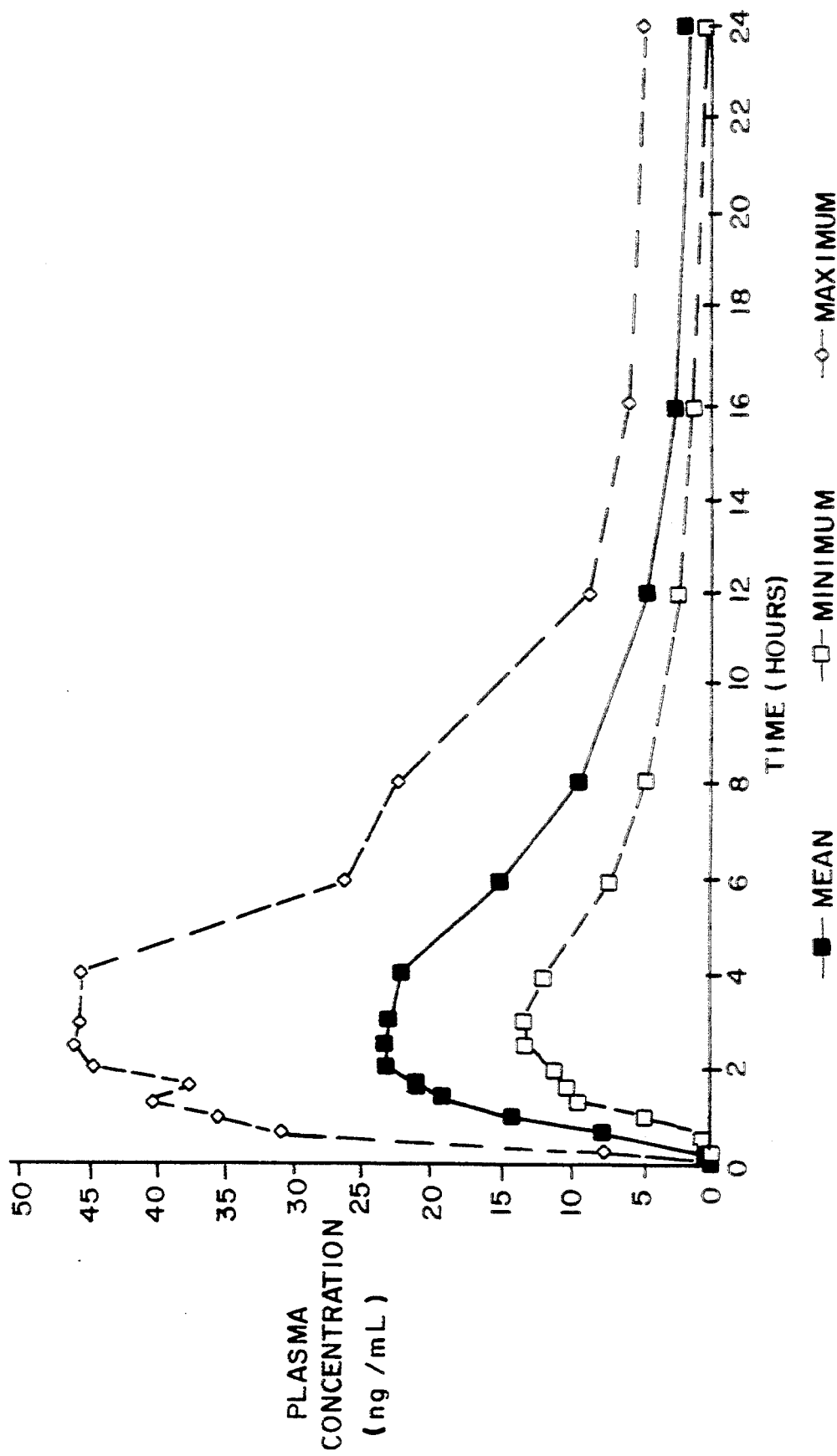
Figure 5:
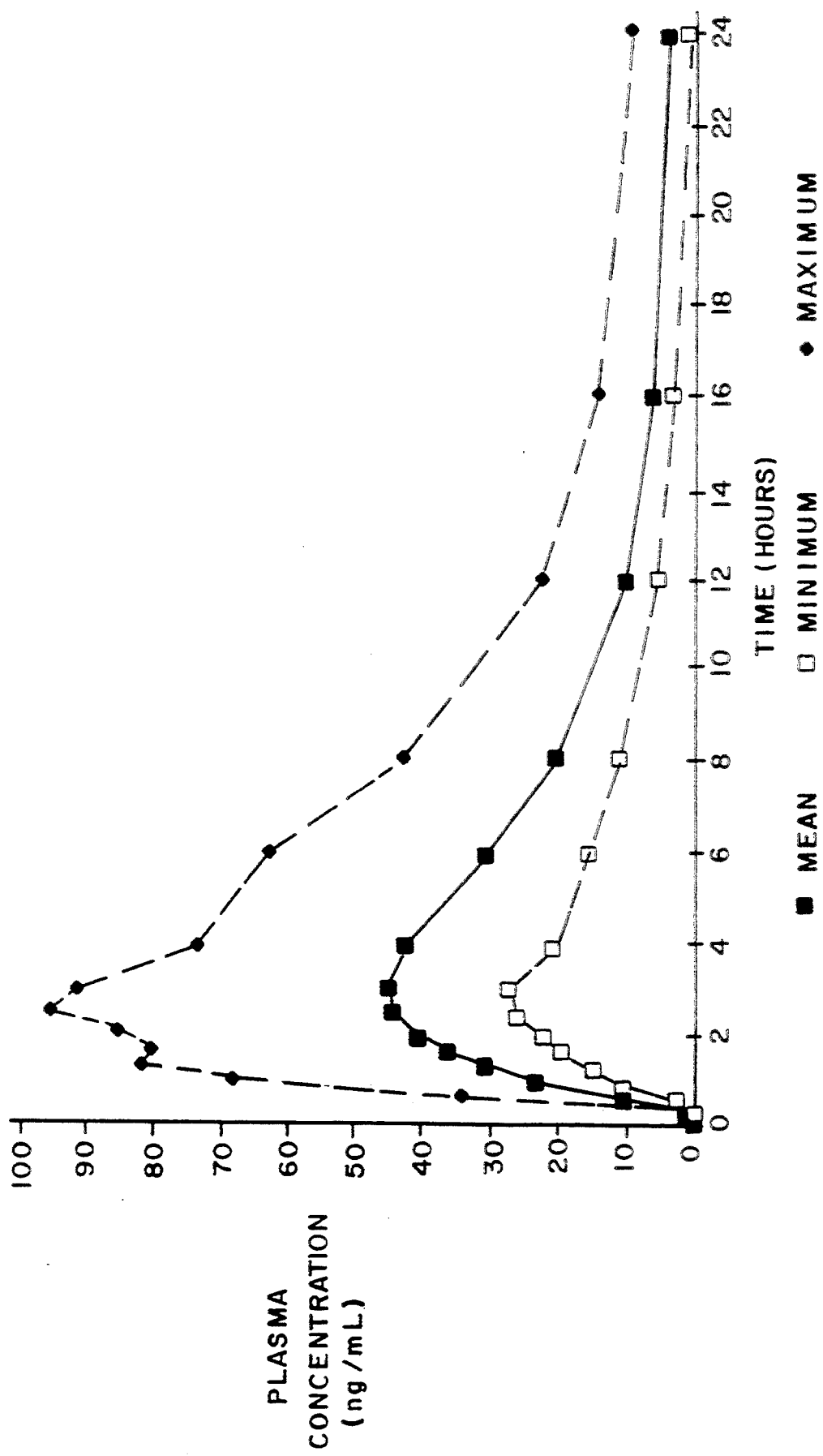
Figure 6:
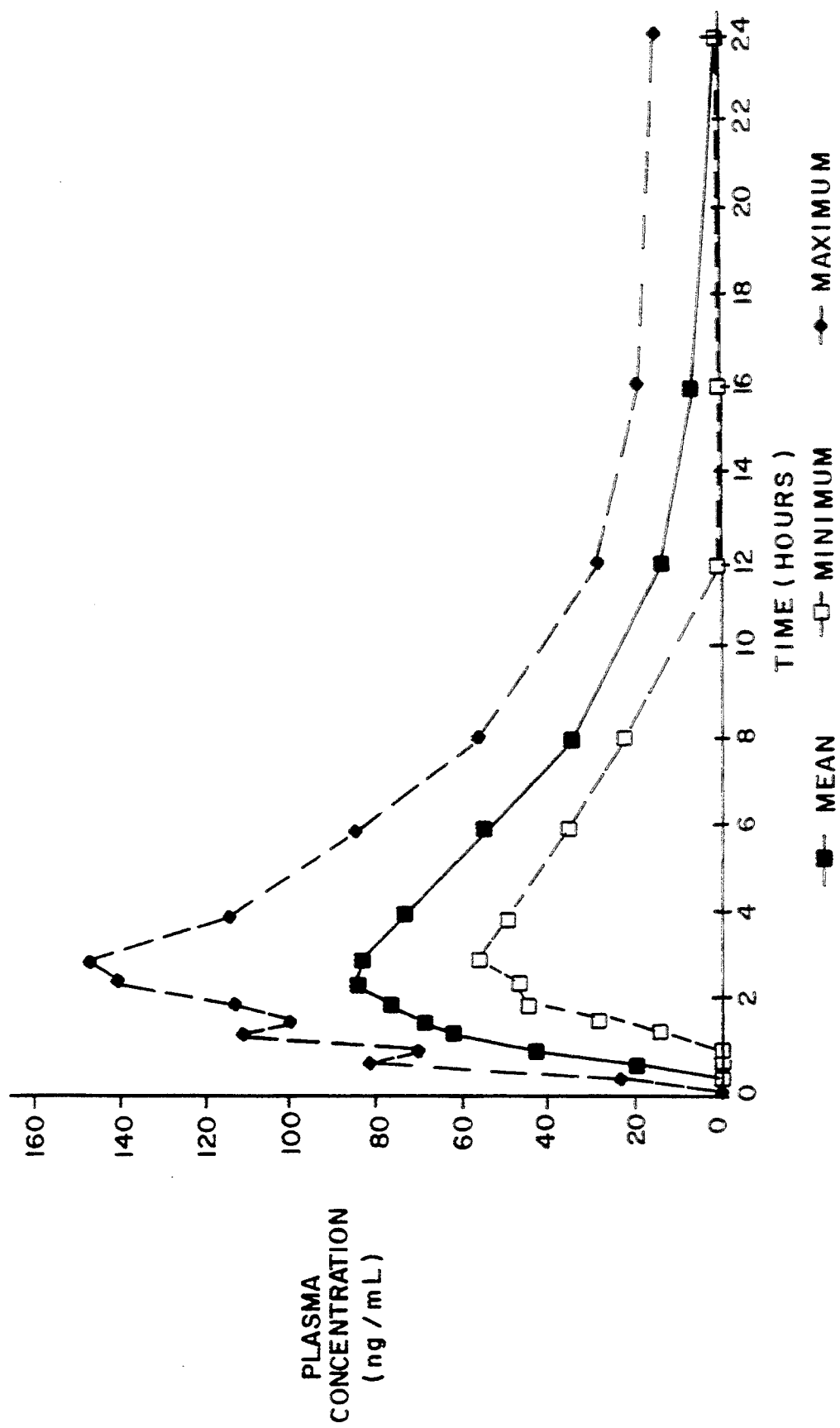

FIG. 4 is a graph showing plasma bupropion (as the free base) concentrations in nanograms/mL in adult male humans following a single dose of two 50 mg bupropion HCl (SR) tablets, divided by two over 24 hours from time of administration provided by the 50 mg tablet example of this invention;

FIG. 5 is a graph showing plasma bupropion as the free base concentrations in nanograms/mL in adult male humans following a single dose of one 100 mg bupropion HCl (SR) tablets over 24 hours provided by the 100 mg tablet example of this invention; and FIG. 6 is a graph showing plasma bupropion (as the free base) concentration in nanograms/mL in adult male humans following a single 150 mg tablet over 24 hours provided by the 150 mg (SR) tablet example of this invention.

DETAILED DESCRIPTION OF THE INVENTION

In order to prepare the controlled sustained release (SR) tablets of this invention, particles of bupropion hydrochloride are preferably blended with microcrystalline cellulose and hydroxypropyl methylcellulose (Methocel ®) to form an admixture of blended powders. A 20 mesh sieve is conveniently used to screen the bupropion hydrochloride particles, cellulose particles and hydroxypropyl methylcellulose particles prior to blending the ingredients. Then the cysteine hydrochloride or glycine hydrochloride is dissolved in water to form a granulating solution. Thereafter, the granulating solution is preferably sprayed onto the blended powders, which are then dried. A lubricant such as magnesium stearate is added and intermixed (blended) with the blended powders having the granulating solution dried thereon. Other suitable fillers include the following: lactose, starch. Microcrystalline cellulose is also preferably added to the product to provide compressibility. Compression of the mixture in a punch and die is then used to form the tablet core.

Thereafter, the tablet (sometimes referred to as the core) is preferably film coated with a color coating such as a Opadry Purple, Opadry Blue or Opadry White for identification, taste masking, and appearance purposes to provide a film coated tablet. The film coating does not substantially affect the release rate of the bupropion hydrochloride from the tablet, since the coating is instant release which rapidly dissolves in the stomach.

The outer film coating is typically 0.03 mm to 0.10 mm in thickness.

In the practice of this invention, for every part by weight of bupropion hydrochloride, the amount of hydroxpropyl methylcellulose is 0.19 to 1.1 and more preferably 0.267 to 0.68 parts by weight and the amount of cysteine hydrochloride or glycine hydrochloride is 0.027 to 0.27 and more preferably 0.05 to 0.162 parts by weight. For example, in a tablet containing 100 mg of bupropion hydrochloride, the amount of hydroxypropyl methylcellulose is 19 mg to 110 mg and most preferably 26.7 to 68 mg and the amount of cysteine hydrochloride or glycine hydrochloride is 2.7 mg to 27 mg and most preferably 5 mg to 16.2 mg.

The surface area to volume of the non film-coated or core portion of the tablets herein is important in maintaining the appropriate controlled sustained release rates.

The ratio of the non film-coated tablet (sometimes referred to as the core) surface area to tablet volume is preferably 3:1 to 25:1 cm$^{-1}$ and more preferably 7:1 to 16:1 cm$^{-1}$ for tablets of 50, 100 and 150 mg bupropion hydrochloride content. For tablets of 50 mg bupropion HCl content the ratio of the tablet surface area to tablet volume is most preferably 13:1 to 16:1 cm$^{-1}$, for 100 mg content the tablet ratio is 9:1 to 12:1 cm$^{-1}$ and for the 150 mg content ratio is 7:1 to 10:1 cm$^{-1}$.

The release rate of bupropion hydrochloride from the sustained release (SR) tablets disclosed (whether or not film coated) herein in distilled water is preferably as follows:

between about 20% and 60% (most preferably 25 and 50%) in 1 hour;

between about 50% and 95% (most preferably 60 and 95%) in 4 hours; and not less than (NLT) about 75% (most preferably NLT 80%) in 8 hours. For the bupropion HCl 50 mg content tablet the release rate of bupropion HCl is preferably about between about 30 and 50% in one hour, between about 70 and 95% in 4 hours and NLT 80% in 8 hours. For the 100 mg bupropion HCl content tablet the release rate is preferably between about 25 and 45% in 1 hour, between about 60 and 85% in 4 hours and not less than (NLT) 80% in 8 hours. With the 150 mg content tablet the release rate is preferably between about 25 and 45% in 1 hour, between about 60 and 85% in four hours and NLT 80% in 8 hours.

The test conditions and apparatus to determine the drug release (dissolution) rates of bupropion hydrochloride are as follows:

Apparatus: USP Rotating Paddle (Apparatus II)
Stirring Rate: 50 rpm
Sample Size: a single unweighted tablet per vessel
Temperature: 37° C.±0.5° C.
Medium for Dissolution of tablet: 900 mL of distilled water.

The test for dissolution (release rates) is performed as specified below in the U.S. Pharmacopoeia under "Drug Release" and the medium is sampled at 1, 4 and 8 hours.

Sample Preparation: Withdraw a measured portion of the dissolution medium not to exceed 10 mL at each sampling point without replacement. Filter the sample through a Zymark 10 micron filter (or equivalent).

Standard Preparation: Accurately weigh approximately 50 mg, 100 mg or 150 mg of Bupropion Hydrochloride Reference Standard and transfer into 900 mL volumetric flask. Dissolve in and dilute to volume with water and mix.

|  | 50 mg | 0.0556 mg burprion HCL per mL |
|---|---|---|
| Nominal Concentration: | 100 mg | 0.111 mg bupropion HCL per mL |
|  | 150 mg | 0.167 mg bupropion HCL per mL. |

Note: Sample and Standard Preparations are stable for 2 days if kept refrigerated.

Procedure: With a suitable system (see System Suitability Test below using the suggested instrumental Conditions listed below chromatograph the Standard (STD) and Sample (SPL) Preparation. Calculate the percent labeled strength bupropion hydrochloride dissolved as shown below. Report the results.

Instrumental Conditions:
Instrument: An appropriate HPLC equipped with a 10-uL sampling loop
Column: BDS Hypersil C1B, 5 micron (50×4.6 mm) column or Supelcosil LC-18DB, 3 micron (33×4.6 mm) column or equivalent
Flow Rate: 2.0 mL/min
Detection: UV, 224 nm 0.1 AUFS or an appropriate AUFS setting
Mobile Phase: Methanol: pH 7.0 phosphate buffer (65:35), appropriately filtered and degassed
System Suitability Test: Replicate injections of the Standard Preparation give relative standard deviations for peak retention times and peak responses not greater than 2 percent. The tailing facto (T,USP) for the bupropion peak is not greater than 2.5.
Phosphate Buffer: Transfer 27.22 g of monobasic potassium phosphate into a 1000-mL volumetric flask. Dissolve in and dilute to volume with water and mix. Transfer 250 mL of this solution into a 1000-mL volumetric flask, add 100 mL of 0.291M sodium hydroxide, dilute to volume with water and mix.

Calculation
Step 1-Determination of Bupropion Hydrochloride Concentration % Nominal Bupropion Hydrochloride [0.0556 mg/mL (50 mg label strength) or 0.111 mg/mL (100 mg label strength) or 0.167 mg/mL (150 mg label strength)]=

$$\frac{SPL\ Pk\ Area}{STK\ Pk\ Area} \times \frac{STD\ Wt}{900} \times \frac{900}{L.s.} \times 100$$

(L.s. Label Strength)

Step II-Sampling Volume Corrections
Perform the following calculations to adjust for sample removal. (Evaporation is insignificant over an 8-hour period when using the Zymate II Automated Dissolution Testing System.) % l.s. Bupropion Hydrochloride released (50 mg/tablet)=

$$\frac{900 - nv}{900}$$

$\times$ % nominal bupropion hydrochloride [sample($n$ + 1)] −

$$\frac{v}{900} \sum_{i=1}^{n}$$ % nominal bupropion hydrochloride [sample ($i$)]

where:
n=number of previous samples taken
v=volume of sample taken each time
These calculations can be performed using the BASIC program "DISTAB."

These Calculations can be performed using the EXCEL spreadsheet "DISSOLUTION PROFILE".

The tablet also preferably includes as other ingredients, e.g., lubricating agents for ease in manufacture and fillers for ease of manufacturing and to bulk the tablet to provide the desired size.

The tablet is also preferably coated with an instant release coating for appearance, taste masking, and product identification e.g. Opadry ® Purple, Blue or White, which will dissolve in the stomach and not substantially affect bupropion hydrochloride release rates and bupropion hydrochloride stability.

Hydroxypropyl Methylcellulose 2910, USP used in the examples, conforms to 28.0 to 30.00% methoxyl substitution and 7.0 to 12.0% hydroxypropoxyl substitution. The preferred nominal viscosity of 2% solution in water is not less than 3,000 centipoise and not more than 5,600 centipoise. It is supplied by Dow Chemical Company, Midland, Mich. as Methocel E4M Premium CR.

Microcrystalline cellulose, NF supplied by FMC Corporation as Avicel PH 102, has an average particle size of 90 micrometers with particle size specification of $8\% \geq 60$ mesh and $45\% \leq 200$ mesh.

Opadry ® Purple YS-1-4845 is supplied by Colorcon, Inc., contains FD&C Red No. 40 Aluminum Lake, hydroxypropyl methylcellulose, titanium dioxide, polyethylene glycol, polysorbate 80, and FD&C Blue No. 2 Aluminum Lake.

Opadry ® Blue YS-1-4282 is supplied by Colorcon, Inc., contains FD&C Blue No. 1 Aluminum Lake, hydroxypropyl methylcellulose, titanium dioxide, polyethylene glycol, and polysorbate 80.

Opadry ® White YS-1-7059 is supplied by Colorcon, Inc., contains hydroxypropyl methycellulose, titanium dioxide, and polyethylene glycol.

All documents mentioned herein are incorporated herein by reference hereto.

Figure 1:
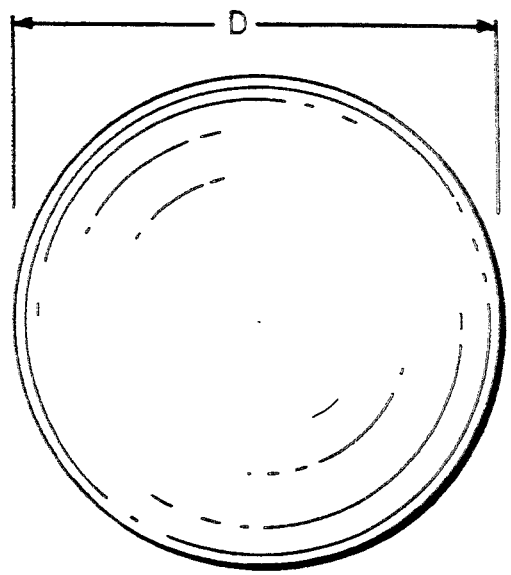
FIG. 1 is a top view of the preferred tablet shape of this invention.
Figure 2:
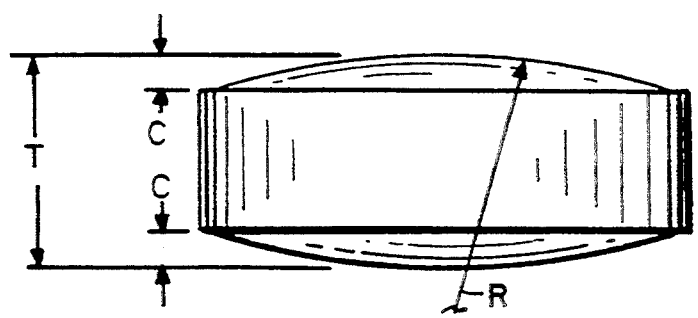
FIG. 2 is a side view of the tablet of FIG. 1.
Figure 3:
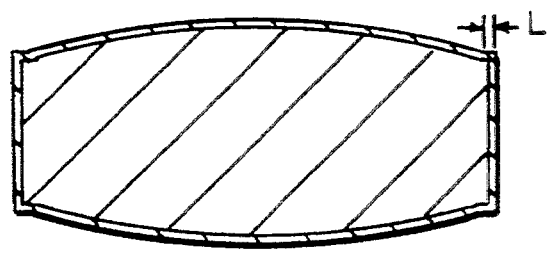
FIG. 3 is a sectional view taken along line 3—3 in FIG. 1.

Reference should now be had to FIGS. 1 to 3 for a description of the preferred form of the biconvex film coated tablets of this invention which contain as the active ingredient (drug) 50 mg, 100 mg or 150 mg of bupropion HCl. The tablet (core) is shown at 10 and the film coating is shown at 11 in FIG. 3.

Tablets having the following dimensions as set forth below for the 50 mg, 100 mg and 150 mg bupropion HCl content tablets in which the letters D (diameter), T (thickness), L (land), C (cup depth) and the R (radius of curvature of the biconvex region) are shown in FIGS. 1 to 3.

|  | 50 mg | 100 mg | 150 mg |
| --- | --- | --- | --- |
| R (inches) | .410 | .4783 | .604 |
| D (inches) | .2913 | .3701 | .4331 |
| C (inches) | .026 | .036 | .039 |
| T (mm) | 3.40 | 4.30 | 4.65 |
| L (inches) | .002 | .003 | .003 |

Reference now should be had to FIGS. 4, 5 and 6 which illustrate plasma bupropion levels, as the free base i.e. the compound bupropion itself (see the Merck Index, Eleventh Edition entry No. 1488) after oral administration to adult males (humans) of 50 mg, 100 mg and 150 mg bupropion HCl film coated tablets of the examples herein. It is to be understood that because of the nature of the film coating, the release rate will be substantially the same whether or not the tablets are film-coated and, therefore, the data is also representative of non film-coated tablets disclosed herein.

In particular, FIG. 4 represents plasma levels (divided by 2) of bupropion after oral dosage with two 50 mg SR tablets in 21 male (human) patients 18 to 40 years of age weighing 132 to 184 lbs. The maximum level shown is detected in the blood plasma at least one of the patients and the minimum being that detected in the blood plasma at least one of the patients and the mean being the average of all measurements of all participants.

The bupropion plasma levels for the 50 mg tablet dosing measured over 24 hours as in this figure were done as described in the radioimmunoassay test set forth in the article Radioimmunoassay And Pharmacokinetic Profile Of Bupropion In The Dog by Robert F. Butz et al. published in the Journal of Pharmacology and Experimental Therapeutics, Vol. 217, No. 3 (1981).

FIG. 5 is a repeat with respect to FIG. 4; however, a single oral dose of a 100 mg SR tablet of this disclosure's example was administered to the same group of males as those tested previously in FIG. 4; however, the bupropion plasma levels were not divided in two. The plasma levels were also measured at the time intervals shown using the test procedure described in the aforementioned Butz et al. article.

FIG. 6 represents oral dosing of 24 male (human) patients, ages 20 to 39 years, weight 136 to 196 lbs. Each of the males was dosed once with a 150 mg bupropion HCl SR tablet and bupropion plasma level measurements were made as shown on the plot of FIG. 6 at the time intervals shown to arrive at the maximum, minimum for any patient and the mean (average) for all patients in the test.

The measurements using the 150 mg tablets of the examples were determined following the procedure described in the article entitled "Determination of Bupropion and Its Major Basic Metabolites in Plasma by Liquid Chromatography with Dual-Wavelength Ultraviolet Detection" by Thomas B. Cooper et al. published in Journal of Pharmaceutical Sciences, Vol. 73, No. 8, August 1984. The results were not divided by two as with the FIG. 4 results.

It should be understood that variations may occur in biological measurements from test to test. It should also be understood that the tablet measurements may change somewhat without departing from the spirit of the invention and that the tablet dimensions will also vary because of variability in materials, manufacturing processes, and tolerance achievable.

It should be understood that the outer coating on the core is preferred in this invention but is not a required feature of the invention herein.

EXAMPLE 1

| EXAMPLE 1 PREPARATION OF 150 MG BUPROPION HCl CONTENT TABLETS | | |
| --- | --- | --- |
|  | mg/tablet | kg/Batch |
| CORE INGREDIENTS | | |
| Bupropion Hydrochloride | 150.0 | 150.0 |
| Microcrystalline Cellulose, NF | 198.5 | 198.5 |
| Hydroxypropyl Methylcellulose 2910, USP | 40.00 | 40.00 |
| Cysteine Hydrochloride, USP | 7.500 | 7.500 |
| Magnesium Stearate, NF | 4.000 | 4.000 |
| Purified Water, USP | qs | qs |
|  | 400.0 mg | |

-continued

EXAMPLE 1
PREPARATION OF 150 MG BUPROPION HCl CONTENT TABLETS

|  | mg/tablet | kg/Batch |
|---|---|---|
| Surface Area To Volume Ratio | 8.818 cm$^{-1}$ | |
| Volume | 0.3656 cm$^3$ | |
| Surface Area | 3.224 cm$^2$ | |
| COATING INGREDIENTS | | |
| Opadry Purple YS-1-4845 | 16.00 | 20.00* |
| Purified Water, USP | qs | 180.00 |
| Carnauba Wax, NF | 0.04 | 0.040 |
| | 416.04 mg | |

Coating thickness ≈ 0.05–0.10 mm
"qs" means sufficient quantity in the examples.
*Includes 25% coverage.

MANUFACTURING PROCEDURE FOR CORE TABLETS 150 MG

1. Using an electric sieve, sift bupropion hydrochloride through a 20 mesh screen into a suitable container.
2. Using an electric sieve, sift microcrystalline cellulose and hydroxypropyl methylcellulose though a 20 mesh screen into a suitable container.
3. Blend for 10 minutes in a suitable blender e.g. a tumble cube blender.
4. While stirring, add the cysteine hydrochloride to the purified water. Mix until the cysteine hydrochloride is dissolved, then strain the solution through a 70 mesh screen.
5. Using the following recommended parameter settings, spray 40 kg of the granulating solution (step 4) onto the blended powders (step 3) using a fluid-bed top-spray granulator, e.g., Glatt WST/G-500:

| Inlet Air Temperature | 40–50° C. |
|---|---|
| Air Volume Setpoint | 40–60% |
| Shake Duration | 10 seconds |
| Shake Interval | 3 minutes |
| Spray Rate | 2000–4000 g/min |
| Atomization Air Pressure | 4 Bar |

Add additional purified water, e.g., approximately 150 kg to impart proper granulation wetness.

6. Dry the granules in the fluid-bed top spray granulator according to the following recommended parameter settings to a granule loss on drying of 0.5–1.5 weight %:

| Inlet Air Temperature | 65–80° C. |
|---|---|
| Air Volume Setpoint | 40–60% |
| Shake Duration | 10 seconds |
| Shake Interval | 3 minutes |

7. Add the magnesium stearate to the dried granule and distribute using a paddle.
8. Sift the granule using a conical mill, e.g, Comil®, fitted with a 0.055 inch screen and operating at 950–1050 RPM.
9. Blend the granules for 5 minutes in a suitable blender, e.g., tumble cube blender.
10. Compress at 400 mg on a rotary press fitted with 11.0 mm round punches and dies; plain upper and lower punches.

| Hardness Range | 6–15 kp |
|---|---|

-continued

| Tablet Thickness | 4.0–5.0 mm |
|---|---|

MANUFACTURING PROCEDURE FOR FILM-COATED TABLETS 150 MG

1. Add the Opadry Purple to the purified water while stirring with an air-driven mixer until the Opadry is evenly suspended.
2. Divide the batch of core tablets into 4 equal portions of approximately 100 kg. Place each portion into a 48 inch perforated coating pan with 2 air atomization spray guns, e.g., Binks, according to the following parameters:

| Pan Speed | 6 RPM |
|---|---|
| Product Bed Temperature | 47–53° C. |
| Air Flow | 1100–1500 CFM |
| Atomization Air | 40–50 PSI |
| Spray Rate | 80–130 g/min per gun |

3. Divide the coating solution into 4 equal portions.
4. Cool the tablets to a product bed temperature of 30°–35° C., then add 10.0 g carnauba wax to each pan while rotating the pan 16 minutes at 6 RPM.

EXAMPLE 2

PREPARATION OF 100 mg BUPROPION HCl CONTENT TABLETS

|  | mg/tablet | kg/Batch |
|---|---|---|
| CORE INGREDIENTS | | |
| Bupropion Hydrochloride | 100.00 | 150.0 |
| Microcrystalline Cellulose, NF | 97.00 | 145.5 |
| Hydroxypropyl Methylcellulose 2910, USP | 54.00 | 81.00 |
| Cysteine Hydrochloride, USP | 16.20 | 24.30 |
| Magnesium Stearate, NF | 2.800 | 4.200 |
| Purified Water, USP | qs | qs |
| | 270.0 mg | |
| Surface Area To Volume Ratio | 10.89 cm$^{-1}$ | |
| Volume | 0.2766 cm$^3$ | |
| Surface Area | 3.013 cm$^2$ | |
| COATING INGREDIENTS | | |
| Opadry ® Blue YS-1-4282 | 10.00 | 20.00* |
| Purified Water, USP | qs | 180.0 |
| Carnauba Wax, NF | 0.02667 | 0.040 |
| | 280.03 mg | |

Coating thickness ≈ 0.05–0.1 mm
qs means sufficient quantity in the examples
*Includes 33.3% overage.

MANUFACTURING PROCEDURE FOR CORE TABLETS 100 mg

1. Using an electric sieve, sift bupropion hydrochloride through a 20 mesh screen into a suitable container.
2. Using an electric sieve, sift microcrystalline cellulose and hydroxypropyl methylcellulose though a 20 mesh screen into a suitable container.
3. Blend for 10 minutes in a suitable blender e.g a tumble cube blender.
4. While stirring, add the cysteine hydrochloride to the purified water. Mix until the cysteine hydrochloride is dissolved, then strain the solution through a 70 mesh screen.
5. Using the following recommended parameter settings, spray 124.3 kg of the granulating solution (step 4)

onto the blended powders (step 3) using a fluid-bed top-spray granulator, e.g., Glatt WST/G-500:

| Inlet Air Temperature | 40–50° C. |
|---|---|
| Air Volume Setpoint | 40–60% |
| Shake Duration | 10 seconds |
| Shake Interval | 3 minutes |
| Spray Rate | 2000–4000 g/min |
| Atomization Air Pressure | 4 Bar |

Add additional purified water, e.g., approximately 110 kg to impart proper granulation wetness.

6. Dry the granules in the fluid-bed top spray granulator according to the following recommended parameter settings to a granule loss on drying of 0.5–1.5 weight %:

| Inlet Air Temperature | 65–80° C. |
|---|---|
| Air Volume Setpoint | 40–60% |
| Shake Duration | 10 seconds |
| Shake Interval | 3 minutes |

7. Add the magnesium stearate to the dried granule and distribute using a paddle.
8. Sift the granule using a conical mill, e.g., Comil®, fitted with a 0.055 inch screen and operating at 950–1050 RPM.
9. Blend the granules for 5 minutes in a suitable blender, e.g., tumble cube blender.
10. Compress at 270 mg on a rotary press fitted with 9.4 mm round punches and dies; plain upper and lower punches.

| Hardness Range | 4–15 kp |
|---|---|
| Tablet thickness | 3.8–4.8 mm |

MANUFACTURING PROCEDURE FOR FILM-COATED TABLETS 100 MG

1. Add the Opadry Blue to the purified water while stirring with an air-driven mixer until the Opadry is evenly suspended.
2. Divide the batch of core tablets into 4 equal portions of approximately 101 kg. Place each portion into a 48 inch perforated coating pan, e.g., Accela-Cota.
3. Divide the coating solution into 4 equal portions.
4. Coat each portion of tablets in the 48 inch perforated coating pan with 2 air atomization spray guns, e.g., Binks, according to the following parameters:

| Pan Speed | 6 RPM |
|---|---|
| Product Bed Temperature | 47–53° C. |
| Air Flow | 1100–1500 CFM |
| Atomization Air | 40–50 PSI |
| Spray Rate | 80–120 g/min per gun |

Coat the tablets until an average weight gain of 10±5 mg per tablet is achieved.
5. Cool the tablets to a product bed temperature of 30°–35° C., then add 10.0 g carnauba wax to each pan while rotating the pan 10 minutes at 6 RPM.

EXAMPLE 3

PREPARATION OF 50 MG BUPROPION HCl CONTENT TABLETS

| | mg/tablet | kg/Batch |
|---|---|---|
| CORE INGREDIENTS | | |
| Bupropion Hydrochloride | 50.0 | 150.0 |
| Microcrystalline Cellulose, NF | 41.50 | 124.5 |
| Hydroxypropyl Methylcellulose 2910, USP | 34.00 | 102.0 |
| Cysteine Hydrochloride, USP | 8.100 | 24.30 |
| Magnesium Stearate, NF | 1.400 | 4.200 |
| Purified Water, USP | qs | qs |
| | 135.0 mg | |
| Surface Area To Volume Ratio | 14.37 cm$^{-1}$ | |
| Volume | 0.1386 cm$^3$ | |
| Surface Area | 1.9914 cm$^2$ | |
| COATING INGREDIENTS | | |
| Opadry White YS-1-7059 | 5.000 | 20.00* |
| Purified Water, USP | qs | 180.0 |
| Carnauba Wax, NF | 0.01333 | 0.040 |
| | 140.0 mg | |

Coating thickness ≈ 0.03–0.07 mm
"qs" means sufficient quantity in the examples
*includes 33.3% overage

MANUFACTURING PROCEDURE FOR CORE OF THE TABLET 50 MG

1. Using an electric sieve, sift bupropion hydrochloride through a 20 mesh screen into a suitable container.
2. Using an electric sieve, sift microcrystalline cellulose and hydroxypropyl methylcellulose though a 20 mesh screen into a suitable container.
3. Blend for 10 minutes in a suitable blender e.g. a tumble cube.
4. While stirring, add the cysteine hydrochloride to the purified water. Mix until the cysteine hydrochloride is dissolved, then strain the solution through a 70 mesh screen.
5. Using the following recommended parameter settings, spray 124.3 kg of the granulating solution (step 4) onto the blended powders (step 3) using a fluid-bed top-spray granulator, e.g., Glatt WST/G-500:

| Inlet Air Temperature | 40–50° C. |
|---|---|
| Air Volume Setpoint | 40–60% |
| Shake Duration | 10 seconds |
| Shake Interval | 3 minutes |
| Spray Rate | 2000–4000 g/min |
| Atomization Air Pressure | 4 Bar |

Add additional purified water, e.g., approximately 120 kg to impart proper granulation wetness.
6. Dry the granules in the fluid-bed top spray granulator according to the following recommended parameter settings to a granule loss on drying of 0.5–1.5 weight %:

| Inlet Air Temperature | 65–80° C. |
|---|---|
| Air Volume Setpoint | 40–60% |
| Shake Duration | 10 seconds |
| Shake Interval | 3 minutes |

7. Add the magnesium stearate to the dried granule and distribute using a paddle.

8. Sift the granule using a conical mill, e.g., Comil, fitted with a 0.055 inch screen and operating at 950-1050 RPM.
9. Blend the granules for 5 minutes in a suitable blender, e.g., tumble cube blender.
10. Compress at 135 mg on a rotary press fitted with 7.4 mm round punches and dies; plain upper and lower punches.

| Hardness Range | 3.5–10 kp |
|---|---|
| Tablet Thickness | 3.0–4.0 mm |

MANUFACTURING PROCEDURE FOR FILM-COATED TABLETS 50 MG

1. Add the Opadry White to the purified water while stirring with an air-driven mixer until the Opadry is evenly suspended.
2. Divide the batch of core tablets into 4 equal portions of approximately 101 kg. Place each portion into a 48 inch perforated coating pan, e.g., Accela-Cota.
3. Divide the coating solution into 4 equal portions.
4. Coat each portion of tablets in the 48 inch perforated coating pan with 2 air atomization spray guns, e.g., Binks, according to the following parameters:

| Pan Speed | 6 RPM |
|---|---|
| Product Bed Temperature | 47–53° C. |
| Air Flow | 1100–1500 CFM |
| Atomization Air | 40–50 PSI |
| Spray Rate | 80–130 g/min per gun |

Coat the tablets until an average weight gain of 5±3 mg per tablet is achieved.
5. Cool the tablets to a product temperature of 30°–35° C., then add 10.0 g carnauba wax to each pan while rotating the pan 10 minutes at 6 RPM.

We claim:

1. A controlled sustained release tablet comprising 25 to 500 mg of bupropion hydrochloride and hydroxypropyl methylcellulose, the amount of hydroxypropyl methylcellulose to one part of bupropion hydrochloride being 0.19 to 1.1 and said tablet having a surface to volume ratio of 3:1 to 25:1 $cm^{-1}$ and said tablet having a shelf life of at least one year at 59° to 77° F. and 35 to 60% relative humidity, said tablet releasing between about 20 and 60 percent of bupropion hydrochloride in water in 1 hour, between about 50 and 90 percent in 4 hours and not less than about 75 percent in 8 hours.

2. The tablet of claim 1, which contains glycine hydrochloride or cysteine hydrochloride in the amount of 0.027 to 0.27 parts by weight of the bupropion hydrochloride.

3. A controlled sustained release tablet comprising an admixture of 25 to 500 mg of bupropion hydrochloride particles, hydroxypropyl methycellulose and glycine hydrochloride or cysteine hydrochloride and having a surface to volume ratio of 3:1 to 25:1 $cm^{-1}$.

4. The tablet of claim 1 wherein an instant release film coating is provided as an outer coating for the tablet.

5. The tablet of claim 1, which contains glycine hydrochloride or cysteine hydrochloride in the amount of 0.05 to 0.162 parts by weight of the bupropion hydrochloride.

6. A controlled sustained release tablet comprising an admixture of 50 to 150 mg of bupropion hydrochloride particles, hydroxypropyl methylcellulose, and cysteine hydrochloride and having a surface to volume ratio of 7:1 to 16:1 $cm^{-1}$.

7. A controlled sustained release tablet comprising an admixture of 50 to 500 mg of bupropion hydrochloride particles, hydroxypropyl methylcellulose and glycine hydrochloride and having a surface to volume ratio of 7:1 to 16:1 $cm^1$.

8. The tablet of claims 6 or 7 having a film coating thereon.

9. A controlled sustained release tablet of claim 1 or 7 comprising about 50 to 150 mg of bupropion hydrochloride, said tablet having surface area to volume ratio of 7:1 to 16:1 $cm^{-1}$.

10. A controlled sustained release tablet of claim 6 or 7 comprising about 50 mg of bupropion hydrochloride, said tablet having a surface area to volume ratio between about 13:1 to 16:1 $cm^{-1}$.

11. A controlled sustained release tablet of claim 6 or 7 comprising about 100 mg of bupropion hydrochloride, said tablet having a surface area to volume ratio of between about 9:1 to 12:1 $cm^{-1}$.

12. A controlled sustained release tablet of claim 6 or 7 comprising about 150 mg of bupropion hydrochloride, said tablet having a surface area to volume ratio between about 7:1 to 10:1 $cm^{-1}$.

13. A controlled sustained release tablet comprising an admixture of 50 mg of bupropion hydrochloride and hydroxyprophyl methylcellulose which after oral administration of a single one of said tablets in adult men produces plasma levels of bupropion as free base ranging between the minimum and maximum levels as shown in FIG. 4 over twenty four hours.

14. A controlled sustained release tablet comprising an admixture of 100 mg of bupropion hydrochloride and hydroxypropyl methylcellulose which after oral administration of a single one of said tablets in adult men produces plasma levels of bupropion as free base ranging between the minimum and maximum levels as shown in FIG. 5 over twenty four hours.

15. A controlled sustained release tablet comprising an admixture of 150 mg of bupropion hydrochloride and hydroxypropyl methylcellulose which after oral administration of a single one of said tablets in adult men produces plasma levels of bupropion as free base ranging between the minimum and maximum levels as shown in FIG. 6 over twenty four hours.

16. The tablet of claims 13, 14 or 15 in which an instant release film coating is provided thereover.

17. A sustained release tablet containing a mixture of (a) 50 mg of bupropion hydrochloride and (b) means for releasing between about 30 and 50 percent of bupropion hydrochloride in one hour, between about 70 and 95 percent in four hours and not less than 80 percent in 8 hours in distilled water said means comprising hydroxypropyl methylcellulose.

18. A sustained release tablet containing a mixture of (a) 100 mg of bupropion hydrochloride and (b) means for releasing between about 25 and 45% of bupropion hydrochloride in one hour, between 60 and 85% in 4 hours and not less then 80% in eight hours in distilled water said means comprising hydroxypropyl methylcellulose.

19. A sustained release tablet containing a mixture of (a) 150 mg of bupropion hydrochloride and (b) means for releasing about between 25 and 45% of bupropion hydrochloride in one hour, between about 60 and 85% in four hours and not less than 80% in eight hours in distilled water said means comprising hydroxypropyl methylcellulose.

* * * * *